(12) United States Patent
Yang et al.

(10) Patent No.: US 12,674,909 B2
(45) Date of Patent: Jul. 7, 2026

(54) GEOLOGICAL HYDROGEN PRODUCTIVITY EVALUATION SYSTEM

(71) Applicant: PUKYONG NATIONAL UNIVERSITY INDUSTRY-UNIVERSITY COOPERATION FOUNDATION, Busan (KR)

(72) Inventors: Min June Yang, Busan (KR); Seong Woo Jeong, Busan (KR); Jin Young Park, Busan (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 691 days.

(21) Appl. No.: 18/316,526

(22) Filed: May 12, 2023

(65) Prior Publication Data

US 2024/0280723 A1     Aug. 22, 2024

(30) Foreign Application Priority Data

Feb. 17, 2023     (KR) ........................ 10-2023-0021581

(51) Int. Cl.
| | |
|---|---|
| *B01J 8/00* | (2006.01) |
| *E21B 43/16* | (2006.01) |
| *E21B 49/08* | (2006.01) |
| *G01N 33/00* | (2006.01) |
| *G01V 9/00* | (2006.01) |
| *G01K 1/04* | (2006.01) |

(52) U.S. Cl.
CPC ............ *G01V 9/007* (2013.01); *E21B 43/168* (2013.01); *E21B 49/087* (2013.01); *G01N 33/0021* (2013.01); *G01K 1/045* (2013.01)

(58) Field of Classification Search
CPC ........................................................ B01J 8/00
See application file for complete search history.

(56) References Cited

U.S. PATENT DOCUMENTS

| | | | | |
|---|---|---|---|---|
| 4,798,717 A | * | 1/1989 | Morency ................... | C22B 1/00 |
| | | | | 423/331 |
| 2023/0102312 A1 | * | 3/2023 | Darrah ...................... | C01B 3/06 |
| | | | | 423/658 |
| 2023/0323756 A1 | * | 10/2023 | Darrah ................ | E21B 41/0064 |

FOREIGN PATENT DOCUMENTS

KR          10-0822824 B1     4/2008

* cited by examiner

*Primary Examiner* — Randy Boyer
(74) *Attorney, Agent, or Firm* — Knobbe, Martens, Olson & Bear, LLP

(57) ABSTRACT

Proposed is a geological hydrogen productivity evaluation system. The system may include a gas injection device configured to inject a reactive gas, a water vapor collecting device configured to collect water vapor generated in the gas injection device when the gas is injected. The system may also include a main reacting device in which a reaction between a solvent and a rock sample, which are loaded into the inside thereof, is performed using the gas supplied from the gas injection device. The system may further include a discharging device through which reactants generated by the reaction in the main reacting device are discharged, and a collecting device configured to collect gas from reactants produced by the reaction by being connected to the discharging device. The system may capture hydrogen from a reactant produced by the reaction of the rock sample in the main reacting device, in the collecting device.

5 Claims, 2 Drawing Sheets

GEOLOGICAL HYDROGEN PRODUCTIVITY EVALUATION SYSTEM

CROSS REFERENCE TO RELATED APPLICATION

The present application claims priority to Korean Patent Application No. 10-2023-0021581, filed Feb. 17, 2023, the entire contents of which is incorporated herein for all purposes by this reference.

BACKGROUND

Technical Field

The present disclosure relates to a geological hydrogen productivity evaluation system and, more particularly, to a geological hydrogen productivity evaluation system capable of evaluating the productivity of hydrogen produced by a reaction between water and rock.

Description of Related Technology

Biological production of hydrogen gas provides a process for minimization of waste and at the same time sustainable fuel production. Hydrogen gas has significant advantages as a clean energy source. Unlike fossil fuels, combustion of hydrogen does not produce carbon dioxide or oxides of nitrogen and sulfur. Hydrogen also has a higher energy yield (for example, about 120 kJ/g) than hydrocarbons (for example, about 44 kJ/g for petroleum). By using hydrogen in fuel cells or reciprocating engines, electricity, water, and heat are obtained as main end products.

SUMMARY

One aspect is a geological hydrogen productivity evaluation system through a water-rock reaction in a geological approach in order to overcome the problems of conventional art.

Another aspect is a geological hydrogen productivity evaluation system, the system including: a gas injection device configured to inject a reactive gas; a water vapor collecting device configured to collect water vapor generated in the gas injection device when the gas is injected; a main reacting device in which a reaction between a solvent and a rock sample, which are loaded into the inside thereof, is performed using the gas supplied from the gas injection device; a discharging device through which reactants generated by the reaction in the main reacting device are discharged; and a collecting device configured to collect gas from reactants produced by the reaction by being connected to the discharging device, wherein the system is configured to capture hydrogen from the reactants produced by the reaction of a rock sample in the main reacting device, in the collecting device.

The gas injection device may use a gas booster for gas injection.

The discharging device may further include a pressure relief device capable of discharging pressure in excess of a set pressure.

The main reacting device and the collecting device each may further include a temperature-pressure control system to control corresponding internal temperature and pressure, wherein the temperature-pressure control system may further include: a thermocouple that is a temperature detection sensor; a temperature controller configured to control a temperature; a pressure transducer configured to regulate a pressure; a pressure indicator controller configured to control a pressure indicator displaying the pressure; and a pressure-reducing valve configured to lower the pressure.

The system may further include a data storage device capable of collecting and storing data generated from the reaction of the rock sample.

As described above, the geological hydrogen productivity evaluation system according to the present disclosure has the following effects.

First, data obtained from reaction experiments can be used as basic data for geological investigations so as to increase hydrogen production.

Second, carbon dioxide ($CO_2$) generated when using fossil fuels is captured to store or sequester in the ground through compression and transportation, and the captured carbon can be utilized where necessary.

Third, it is possible to secure safety by preventing accidents caused by an occurrence of excessive pressure.

BRIEF DESCRIPTION OF THE DRAWINGS

The above and other objectives, features, and other advantages of the present disclosure will be more clearly understood from the following detailed description when taken in conjunction with the accompanying drawings.

DETAILED DESCRIPTION

Hydrogen gas is attracting attention as a future energy source because of its ecologically friendly characteristics and is manufactured through biological production methods.

Korean Patent No. 10-0822824 discloses Flat Vertical Parallelepiped-type Photobioreactor Made with Transparent Acrylic Plastic for Biological Hydrogen Production.

The flat vertical parallelepiped-type photobioreactor made with transparent acrylic plastic for biological hydrogen production of the conventional art is configured to make photosynthesis of microorganisms active by providing constant light to the entire inside of an incubator that is a rectangular parallelepiped made of a transparent material.

However, such related art is a technology for biological hydrogen production using microorganisms and has a disadvantage in that it is inefficient by being produced by a process that consumes a lot of energy.

Accordingly, in order to overcome the disadvantages of the conventional biological hydrogen production technology using microorganisms, there is a demand for a non-biological hydrogen production technology and a technology capable of allowing the hydrogen production efficiency to be known.

The foregoing is intended merely to aid in the understanding of the background of the present disclosure and is not intended to mean that the present disclosure falls within the purview of the related art that is already known to those skilled in the art.

Embodiments described below are provided so that those skilled in the art may easily understand the technical idea of the present disclosure, and the present disclosure is not limited thereto. In addition, matters represented in accompanying drawings are schematically illustrated to easily explain the embodiments of the present disclosure and may be different from the forms actually implemented.

It should be understood that when a component is referred to as being connected or linked to another component, it may be directly connected or linked to the other component, but other components may exist in the middle.

Figure 1:
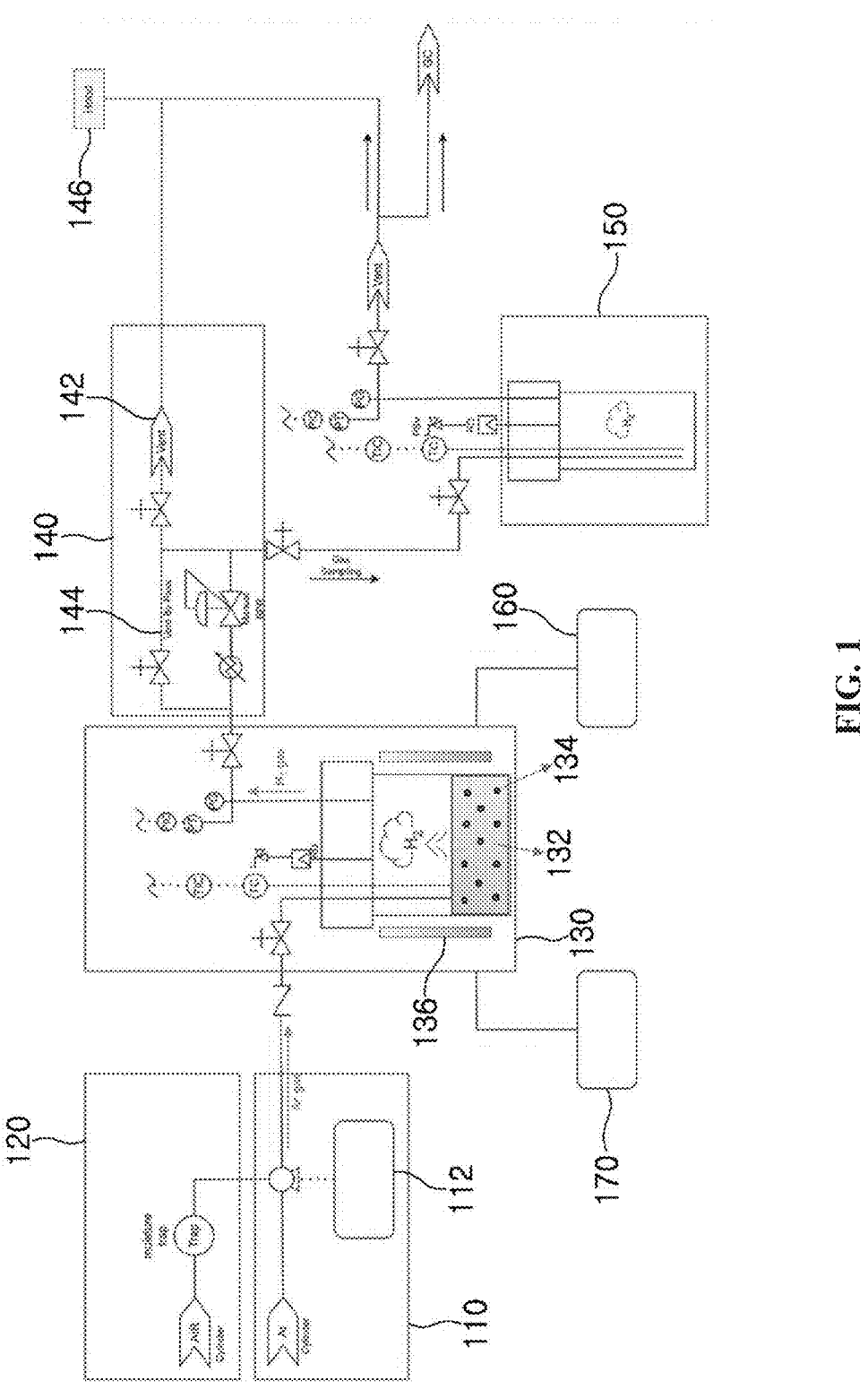
FIG. 1 is a mimetic diagram schematically showing an overall configuration of a geological hydrogen productivity evaluation system according to an embodiment of the present disclosure.
Figure 2:
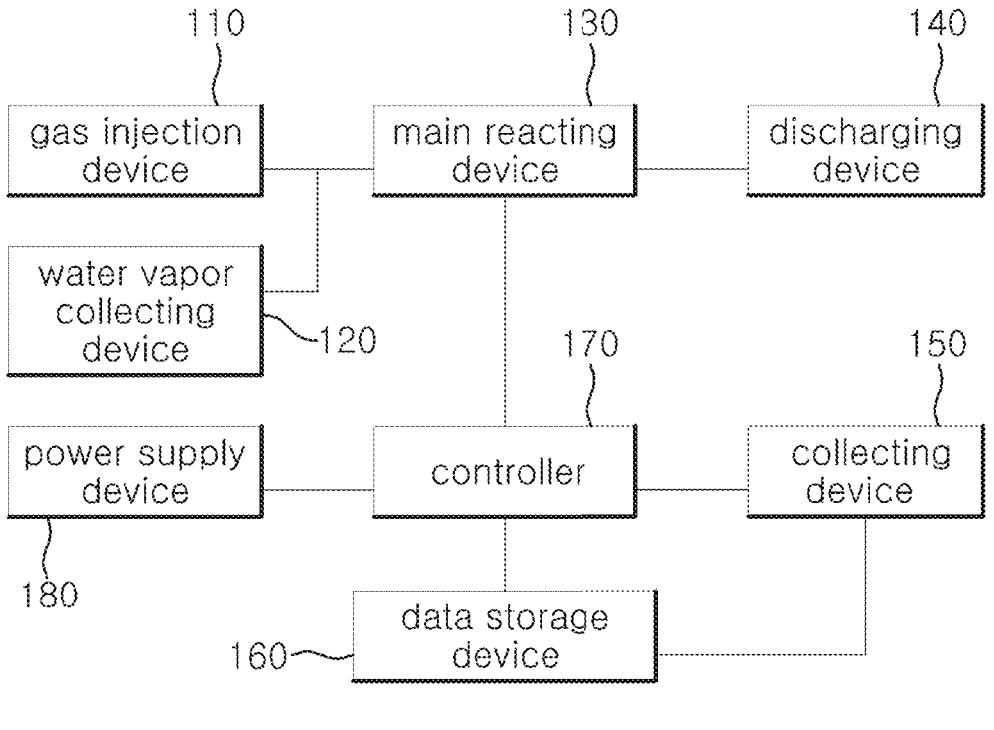
FIG. 2 is a block diagram of the overall configuration of the geological hydrogen productivity evaluation system according to the embodiment of the present disclosure.

FIG. 1 is a mimetic diagram schematically showing an overall configuration of a geological hydrogen productivity evaluation system according to an embodiment of the present disclosure, and FIG. 2 is a block diagram of the overall configuration of the geological hydrogen productivity evaluation system according to the embodiment of the present disclosure.

With reference to FIGS. 1 and 2 together, the geological hydrogen productivity evaluation system according to the embodiment of the present disclosure includes: a gas injection device 110 configured to inject a reactive gas; a water vapor collecting device 120 configured to collect water vapor generated in the gas injection device 110 when the gas is injected; a main reacting device 130 in which a reaction, which generates hydrogen by the reaction of a solvent and a rock sample, which are loaded into the inside thereof, is performed by using the gas supplied from the gas injection device 110; a discharging device 140 through which reactants generated in the main reacting device 130 are discharged; and a collecting device 150 configured to collect the gas generated by the reaction. Here, the reactants are gases and fluids containing hydrogen, and low-temperature and low-pressure reactants may be hydrogen captured with low temperature and low pressure from the reactants.

In one specific example, the gas injection device 110 injects the reaction gas to react with the solvent and rock into the main reacting device 130. The gas injection device 110 is a device configured to inject the gas (for example, argon, carbon dioxide, and the like) into the main reacting device 130.

The gas injection device 110 uses a gas booster 112 for gas injection.

The gas booster 112 is configured to have a piston, which is accommodated inside a cylinder to be driven by a motor, to compress the gas inside the cylinder using a gas booster controller, and the motor of the gas booster is driven by a pneumatic or hydraulic assembly. The gas booster 112 according to the present disclosure may be, for example, an air pump.

In the gas injection device 110, the gas booster 112 may have the maximum injection pressure allowed up to 2400 bar exceeding the pressure of the main reacting device 130 in order to prevent the reverse flow of the injection fluid. Through this, an environment in which fluid can be injected at various pressures is configured.

The water vapor collecting device 120 is configured to collect vapor generated in the gas injection device 110 when the gas is injected.

The water vapor collecting device 120 is configured to collect water vapor from the injection gas supplied in a wet state, thereby reducing errors generated in the reaction experiment.

Gas is supplied from the gas injection device 110 to the main reacting device 130. In addition, the solvent 132 and the rock sample 134, whose weight is measured, are loaded into the main reacting device 130, and a reaction, in which hydrogen is generated by a chemical reaction, occurs.

Here, the solvent 132 may include seawater, water, rainwater, and the like. In addition, the rock sample 134 may include sedimentary rock, metamorphic rock, igneous rock, volcanic rock, quartz, plagioclase, orthoclase, biotite, muscovite, and the like.

The main reacting device 130 may be provided with a rock sample amount controller capable of controlling and supplying the amount of rock sample loaded thereinto.

The main reacting device 130 may include: a vessel, which is a reaction vessel in which an accommodation space made of Hastelloy is provided, to secure durability against a high-temperature and high-pressure test environment; and a pressure safety valve (PSV), which is a pressure-reducing valve having a fitting made of stainless steel and lowering pressure. Hastelloy material may secure durability against pH change (weak acidity-weak basicity) of liquid sample caused by water-rock reaction. The vessel may be sealed by a cover covering the top.

In addition, as the pressure safety valve is mounted, the risk of rupture due to corrosion of the vessel that may occur during the experiment may be minimized.

According to the present disclosure, the experiment may take up to 9000 hours, so the main reacting device 130 and the collecting device 150 each further include a temperature-pressure control system, wherein the temperature-pressure control system includes, for example, a thermocouple (TC), which is a temperature detection sensor, configured to detect the internal temperature of each of the main reacting device 130 and the collecting device 150, a temperature controller (Temperature Indicating Controller (TIC)) configured to control the internal temperature of each of the main reacting device 130 and the collecting device 150, a pressure transducer (PT) configured to regulate the internal pressure of each of the main reacting device 130 and the collecting device 150, a pressure indicating controller configured to control the pressure indicator, and a pressure gage (PG) configured to measure pressure, thereby being allowed to monitor changes in temperature-pressure inside the vessel that occur during the experiment and respond to the changes occurred. Components of the temperature-pressure control system may be provided on an upper portion of a cover covering a vessel serving as a reacting vessel.

The discharging device 140 is configured to discharge the reactants generated in the main reacting device 130. In addition, when the injection of the fluid into the main reacting device 130 continues, overpressure in which a pressure higher than a designated pressure is generated, that is, a pressure exceeding phenomenon may occur.

The discharging device 140 further includes a pressure relief device 144 in the bypass path so as to discharge pressure in excess of a set pressure and is a device that may automatically discharge as much as the exceeding pressure through the vent 142. When the injection of a fluid or gas as a reactant continues during the course of an experiment, an overpressure phenomenon in which a higher pressure than a designated pressure is generated may occur. The discharging device 140 is a device capable of automatically discharging as much as the exceeding pressure through the outlet 142 when excessive pressure is generated. In such a process, when the experiment has to be stopped due to an unexpected situation, the discharging device 140 is a device directly connected to a termination system that is capable of discharging all the fluid injected into the inside thereof. The discharged gas is discharged through the exhaust port of the hood 146 in which the present system is installed, so the safety of the laboratory may be secured.

The collecting device 150 is a device configured to collect low-temperature and low-pressure reactants, for example, hydrogen gas, generated by the reaction performed in the main reacting device 130.

The fluid coming out of the main reacting device 130 moves in a state of maintaining the internal temperature and pressure of the main reacting device 130, so sampling right away is difficult. To solve this problem, a reservoir tank or a sampling vessel provided with a receiving space therein may be installed, whereby the temperature and pressure of the fluid to be sampled may be lowered. To this end, the collecting device 150 may include a pressure-reducing valve that lowers the temperature and pressure.

According to the present disclosure, the system further includes a data storage device 160 capable of collecting and storing data generated in the chemical reaction experiment and data information on the collected gas.

In addition, the geological hydrogen productivity evaluation system according to the embodiment of the present disclosure further includes a controller 170 including a microcontroller configured to calculate and process data to control the entire operation and experiment, and a power supply device 180 configured to supply power.

In the experimental process of the geological hydrogen productivity evaluation system according to the present disclosure, a reaction gas, for example, argon gas, is injected into the main reacting device 130 using the gas injection device 110. The inner space of the main reacting device 130 allows the pressure and temperature to be raised to high pressure and high temperature for the reaction.

A method of increasing the pressure inside the vessel of the main reacting device 130 is possible to be implemented through the injection of fluid or gas, and an electronic heater 136 outside the vessel of the main reacting device 130. For example, when the temperature is raised to 450° C., the pressure inside the vessel of the main reacting device 130 increases due to the increase in temperature. In this case, the pressure to be raised rises within the durability range of the equipment. The pressure obtained by subtracting as much as the pressure, at a time when the temperature inside the vessel of the main reacting device 130 reaches 450° C., from the target pressure value is injected using the gas booster 112, and thus the pressure inside the vessel is finally reached 500 bar.

The system is configured to allow a reactant generated in the main reacting device 130 to be moved through the discharging device 140 and obtained in a state in which the temperature and pressure are lowered in the collecting device 150.

Here, reaction experiment information such as hydrogen data and the like obtained through the reaction experiments is stored in the data storage device 160 and converted into a database. Data obtained from such reaction experiments is used as basic data for geological investigations.

Therefore, the geological hydrogen productivity evaluation system according to the present disclosure simulates the earth's internal environment, whereby the gas generated in the main reacting device 130 is discharged through the discharging device 140, and the hydrogen gas generated by the chemical reaction is collected in a state where the temperature and pressure are lowered through the collecting device 150.

In addition, the system further includes a data storage device 160 capable of collecting and storing data generated in the reaction experiment, thereby collecting and saving the data acquired in the data storage device 160 along with the information obtained through the collection device 150.

Thus, the geological hydrogen productivity evaluation system according to the present disclosure system may be used as basic data for geological investigations by data obtained from reaction experiments, thereby increasing hydrogen production, storing or sequestering the carbon dioxide ($CO_2$) into the ground passing through a process of compression and transportation by capturing carbon dioxide generated when using fossil fuels, and utilizing the captured carbon where needed. In addition, it provides the effect of securing safety by preventing an accident caused by the occurrence of excessive pressure.

Those skilled in the art to which the present disclosure pertains will understand that the present disclosure may be embodied in other specific forms without changing the technical spirit or essential features thereof. Therefore, the embodiments described above are merely selected among various possible embodiments and presented to the most exemplary embodiments to help those skilled in the art to understand, and the technical spirit of the present disclosure is not necessarily restricted or limited only by the presented embodiments. In addition, it should be noted that various changes, additions, and modifications are possible within a range that does not deviate from the technical spirit of the present disclosure, and other equivalent embodiments are possible.

What is claimed is:

1. A geological hydrogen productivity evaluation system, the system comprising:
   a gas injection device configured to inject a reactive gas;
   a water vapor collecting device configured to collect water vapor generated in the gas injection device in response to the gas being injected;
   a main reacting device in which a reaction between a solvent and a rock sample, which are loaded into the inside thereof, is configured to be performed using the gas supplied from the gas injection device;
   a discharging device through which reactants generated by the reaction in the main reacting device are configured to be discharged; and
   a collecting device configured to collect gas from reactants produced by the reaction by being connected to the discharging device,
   wherein the system is configured to capture hydrogen from the reactants produced by the reaction of a rock sample in the main reacting device, in the collecting device.

2. The system of claim 1, wherein the gas injection device is configured to use a gas booster for gas injection.

3. The system of claim 1, wherein the discharging device further comprises a pressure relief device configured to discharge pressure in excess of a set pressure.

4. The system of claim 1, wherein the main reacting device and the collecting device each further comprise a temperature-pressure control system to control corresponding internal temperature and pressure,
   wherein the temperature-pressure control system further includes:
      a thermocouple comprising a temperature detection sensor;
      a temperature controller configured to control a temperature;
      a pressure transducer configured to regulate a pressure;
      a pressure indicator controller configured to control a pressure indicator displaying the pressure; and
      a pressure-reducing valve configured to lower the pressure.

5. The system of claim 1, further comprising:

a data storage device configured to collect and store data generated from the reaction of the rock sample.

\* \* \* \* \*